United States Patent [19]

Ward, Jr. et al.

[11] Patent Number: 5,403,721
[45] Date of Patent: Apr. 4, 1995

[54] PRECIPITATE TEST FOR MICROORGANISMS

[75] Inventors: N. Robert Ward, Jr.; John P. DesRosier, both of Seattle; Elliott D. Marshall, III, Renton; Judith Ford, Bothell; Nancy J. S. Mallinak, Seattle, all of Wash.

[73] Assignee: BioControl Systems, Inc., Bothell, Wash.

[21] Appl. No.: 51,569

[22] Filed: Apr. 21, 1993

Related U.S. Application Data

[63] Continuation of Ser. No. 865,694, Apr. 8, 1992, abandoned, which is a continuation of Ser. No. 655,175, Feb. 12, 1991, abandoned, which is a continuation of Ser. No. 345,033, Apr. 27, 1989, abandoned.

[51] Int. Cl.$^6$ .................... C12Q 1/00; C12Q 1/08; C12Q 1/10
[52] U.S. Cl. .................... 435/34; 435/4; 435/38; 435/288; 435/296; 435/805; 435/970; 436/533; 436/534
[58] Field of Search .................... 435/4, 38, 34, 288, 435/296, 805, 970; 436/533, 534

[56] References Cited

U.S. PATENT DOCUMENTS

| | | | |
|---|---|---|---|
| 3,856,628 | 12/1974 | Sbarra | 435/34 |
| 3,862,011 | 1/1975 | Smith | 435/24 |
| 3,881,993 | 5/1975 | Freake et al. | 435/294 |
| 3,957,584 | 5/1976 | Kronish et al. | 435/4 |
| 4,018,653 | 4/1977 | Mennen | 435/295 |
| 4,278,763 | 7/1981 | Berger et al. | 435/23 |
| 4,390,622 | 6/1983 | Cartwright . | |
| 4,556,636 | 12/1985 | Belly et al. | 435/34 |
| 4,753,876 | 6/1988 | Hemming et al. | 435/34 |
| 4,767,702 | 8/1988 | Cohenford | 435/24 |
| 4,803,162 | 2/1989 | Smith et al. | 435/36 |
| 4,812,409 | 3/1989 | Babb et al. | 435/7.32 |
| 4,824,640 | 4/1989 | Hildenbrand et al. | 436/165 |
| 4,830,970 | 5/1989 | Madaus et al. | 435/296 |
| 4,923,804 | 5/1990 | Ley et al. | 435/38 |

FOREIGN PATENT DOCUMENTS

| | | |
|---|---|---|
| 0122028 | 10/1984 | European Pat. Off. . |
| 0128521 | 12/1984 | European Pat. Off. . |
| 0018825 | 11/1990 | European Pat. Off. . |
| 2031949 | 4/1980 | United Kingdom . |
| 2050418 | 1/1981 | United Kingdom . |
| 2093994 | 9/1982 | United Kingdom . |

OTHER PUBLICATIONS

Frampton et al., "Evaluation of the beta-glucuronidase substrate 5-bromo-4-chloro-3-indolyl-beta-D-glucuronide (X-GLUC) in a 24-hour direct plating method for *Escherichia coli*," *J. Food Prot.* 51:402–404, 1988.

Ley et al., "Use of indoxyl-beta-D-glucuronide for the enumeration of *Escherichia coli*," *Ann. Meet. Amer. Soc. Microbiol.*, Abstract Q35:288, 1988.

Watkins et al., "A novel compound for identifying *Escherichia coli*," *Appl. Environ. Microbiol.* 54:1874–1875, 1988.

Markavyan et al *Bioorg Khim* 13(2): 263–5, 1987.

*Primary Examiner*—Michael G. Wityshyn
*Assistant Examiner*—Jane Williams
*Attorney, Agent, or Firm*—Seed and Berry

[57] ABSTRACT

There is disclosed an improved method for testing for the presence of a particular microorganism or group of microorganisms characterized by a particular enzyme. The method uses a dye-forming substrate throughout a polymer matrix or on the surface of a solid support member that forms a colored precipitate when cleaved by the enzyme. The precipitate is concentrated to the polymer matrix and/or solid support member to create a visible reaction product, wherein the amount of dye-forming substrate needed is independent of the sample size. The present invention further comprises an enzyme indicator device comprising a dye-forming substrate throughout a polymer system or on the surface of a solid support member.

15 Claims, 1 Drawing Sheet

PRECIPITATE TEST FOR MICROORGANISMS

CROSS-REFERENCE TO RELATED APPLICATION

This application is a continuation of U.S. application Ser. No. 07/865,694 filed Apr. 8, 1992, now abandoned, which is a continuation of U.S. application Ser. No. 07/655,175, filed Feb. 12, 1991, now abandoned, which is a continuation of U.S. application Ser. No. 07/345,033, filed Apr. 27, 1989, now abandoned.

TECHNICAL FIELD OF THE INVENTION

The present invention relates to an improved method for assaying for a particular microorganism or group of microorganisms wherein the particular microorganism or group of microorganisms are characterized by the presence of a particular enzyme. The assay uses a dye-forming substrate within a polymer matrix or on the surface of a solid support. The dye precipitates when cleaved by the enzyme. The present invention further comprises an enzyme indicator device comprising a dye-forming substrate, polymer system, and a solid support.

BACKGROUND OF THE INVENTION

Human gastrointestinal disease can be caused by a variety of microorganisms. Common vehicles for infection are contaminated foods and water. To reduce the incidence of such disease, foods and water destined for human consumption are routinely tested for their sanitary quality. Instead of testing for a multitude of different enteric pathogens, laboratories test for the presence of indicator organisms. Coliform bacteria are typically used as the primary indicators of sanitary quality because they are commonly associated with the gastrointestinal tracts of warm-blooded animals. The presence of coliform bacteria, especially *Escherichia coli*, in high numbers in foods or water suggests that there may be fecal contamination, and contraindicates human consumption.

Coliform bacteria are distinguished from other organisms and from their close relatives in the family Enterobacteriaceae by their ability to ferment lactose to acidic and gaseous ($CO_2$ and $H_2$) end products. Certain non-coliform bacteria may ferment lactose to the same end products, but the growth of these organisms in the coliform assay is usually minimized or prevented by the selective properties of the bacteriological media used for testing.

Typically, the presence of coliform bacteria in a sample is determined by adding the material to a liquid bacteriological growth medium and incubating the mixture at a temperature which is conducive to bacterial growth. Incubation of the mixture of sample and growth medium is important because the assay must detect low levels of coliform bacterial contamination in the sample. Incubation of the mixture results in the multiplication of coliforms to a level of approximately $10^6$ to $10^8$ cells per milliliter of culture, wherein their presence may be detected by any of a number of techniques. The variety of different liquid bacteriological growth media which have been used for coliform detection share two common properties: they contain the disaccharide lactose and they also contain chemical agents which selectively inhibit the growth of non-coliform microorganisms. Selection is important because the sample invariably contains a variety of microorganisms, and the success of the assay depends on the coliforms not being overgrown by the non-coliforms.

Coliform assays can be performed using either solid or liquid media. Assays which employ a solid medium allow a viable cell count. Sample is added to the solid medium and discrete colonies of coliforms are enumerated. Alternatively, samples may be added to liquid media. Coliforms are detected through the formation of characteristic metabolic end products. The liquid medium format may be qualitative or quantitative. The liquid medium format is preferred for samples containing fewer coliforms (e.g., less than 10 organisms per milliliter), or samples containing particulate material (e.g., food or dairy samples) which obscures colony visualization.

Most coliform assays in a broth or agar take place in two discrete stages: presumptive and confirmed. First, a presumptive assay provides an indication of possible coliform presence. In the confirmed stage, presumptively positive cultures or typical colonies are subcultured into a second, more selective medium. In principle, the confirmed medium eliminates false positive results. Together, the two stages of the assay require 48 to 96 hours for completion. Therefore, there is a need in the art to provide accurate results in a more timely manner.

Generally, detection is based upon the end products of metabolic pathways of coliform bacteria. For example, acid production by coliform bacteria is generally detected through the incorporation of pH indicators in the medium. Acid formation can be detected by a change in color from purple to yellow of the indicator bromocresol purple in a liquid medium such as Clarke's medium. Acid production is detected by the formation of colonies which are dark-centered due to the reaction between the acid and the indicator neutral red in a solid medium such as violet red bile agar (VRBA) and MacConkey agar.

Further, gaseous end products are usually detected by the presence of gas bubbles in a liquid. Gas bubbles may be entrapped in a smaller, inverted test tube or an inverted vial within the culture tube or in a special portion of the culture device. For example, the BioControl ColiTrak TM product entraps gas bubbles in a dome associated with the top portion of the device. Petrifilm TM (3M), with a solid growth medium, entraps gas bubbles in close proximity to a bacterial colony. Alternatively, gaseous end products may be detected by nonvisual means such as by electrochemical detection of hydrogen, by radiometric detection of $^{14}CO_2$ released from the fermentation of radiolabelled lactose, or by impedimetric or gas chromatographic detection of organic compounds produced during fermentation.

An alternative approach to coliform detection is based upon the detection of coliform-associated enzyme activity rather than metabolic end products. Generally, an enzyme assay approach can yield quantitative estimates for coliform bacteria comparable to confirmatory results using lengthy culture testing procedures. The enzyme beta-galactosidase is a bacterial enzyme used for the fermentation of lactose. Beta-galactosidase hydrolyzes lactose to its component sugars glucose and galactose. Coliform bacteria typically express this enzyme. For example, Warren et al., *Appl. Environ. Microbiol.* 35:136–41, 1978, refers to a coliform testing method which uses the chromogenic beta-galactosidase substrate, o-nitrophenyl-beta-D-galactoside (ONPG), for quantitating fecal coliforms in water. In Warren et al., the time of appearance of the yellow reaction product o-nitrophenol (ONP) is inversely related to the initial concentration of coliforms in the test sample.

The product Colilert ™ (Access Medical) uses the ONPG enzyme indicator for detecting coliforms in drinking water. The water sample is used to solubilize a basal growth medium containing ONPG. Beta-galactosidase from the bacteria growing in the culture hydrolyzes the ONPG to produce galactose, which serves as the sole carbon and energy source for growth. ONP formation indicates enzyme activity. After 24 hours of incubation, the presence of a yellow color throughout the liquid culture of 10 milliliters signifies that coliform bacteria were present in the water sample.

The fluorogenic beta-galactosidase substrate fluorescein-beta-D-galactoside is another indicator of activity. Cundell et al., *Proc. Water Reuse Symp.* 3:1895–99, 1979, refers to an assay incubating coliform bacteria in a medium containing the fluoresceinobeta-D-galactoside. Coliform bacteria are determined quantitatively by flow cytometry. The fluorescein moiety of the substrate becomes concentrated within the cell after cleavage by beta-galactosidase and imparts fluorescence to the cells under ultraviolet illumination. U.S. Pat. No. 4,242,447 refers to a fluorescent assay for enumerating coliforms using a fluorogenic substrate. Specifically, U.S. Pat. No. 4,242,447 refers to a process emulsifying a water sample and a fluorogenic substrate with an oil to form oil droplets containing coliform bacteria. Beta-galactosidase activity cleaves the fluorogenic substrate and forms a fluorescent oil droplet which is counted in a fluorescence detector. Cundell et al., *Dev. Ind. Microbiol.* 20:571–77, 1979, refers to a similar technique that yields oil-encapsulated cells on a microscope slide. Fluorescent droplets are counted under a fluorescence microscope. The Cundell method has been used with sewage samples. The sensitivity of the Cundell method is $10^5$ cells per milliliter.

The bacterium, *E. coli*, is a coliform which may be assayed separate and apart from the coliform bacteria. *E. coli* presence is considered to be a more reliable indicator of fecal contamination. Additionally, certain strains of *E. coli* are pathogenic for humans and animals. The standard *E. coli* detection method subcultures positive presumptive cultures into EC broth and incubates at 45.5° C. Gas-positive EC cultures are then streaked onto a differential agar medium. The isolates are identified by biochemical characterization.

*E. coli* is a relatively unique organism by possessing the enzyme beta-glucuronidase. Consequently, the fluorogenic substrate 4-methylumbelliferyl-beta-D-glucuronide (MUG) is used to detect *E. coli* in food and water samples. The *E. coli* detection procedure consists of inoculating cultures and incubating by standard methods in the presence of MUG. Fluorescence which develops during 24 hours incubation indicates the presence of *E. coli* because beta-glucuronidase from *E. coli* cleaves MUG to a fluorescent product. Thus, the use of MUG-containing media can shorten the detection time for *E. coli*. Unfortunately, MUG is an expensive reagent and large sample sizes, such as water samples, require large quantities of MUG and make the test prohibitively expensive. Currently, the recommended concentration of MUG is 50–100 micrograms per milliliter of final culture. Typical volumes for food and water tests are 90 and 100 milliliters respectively. Thus, the cost of the MUG reagent makes it unattractive for food testing and for use in the PA type of water testing.

One can assay for beta-galactosidase and beta-glucuronidase activities as a means for determining the presence of coliforms and *E. coli*, respectively. Enzyme detection assays offer advantages over the detection of fermentation end products. First, the enzyme assay approach is more sensitive. One enzyme can cleave many substrate molecules. Each molecule of substrate cleaved by an enzyme yields a fluorescent or colored reporter product. Therefore, the signal is amplified by an enzyme. With certain substrates, as few as $10^4$ metabolically active cells can yield a signal within 24 hours.

By contrast, it takes approximately $10^7$ to $10^8$ metabolically active cells to produce a visible gas bubble within 24 hours, because beta-galactosidase cleavage of lactose does not result in stoichiometric amounts of acid and gas end products due to physiological regulation of metabolism. The majority of the carbon in the lactose molecule is incorporated into cellular biomass and is not used to regenerate oxidized AND during fermentation. The bacterial fermentation enzymes responsible for acid and gas production are at the end of the fermentation pathway and are tightly regulated. For instance, pyruvate-formate lyase is inactive under aerobic conditions and is activated only when the culture becomes anaerobic. Formate dehydrogenase, a key enzyme in gas production, is not synthesized in the presence of oxygen or when the culture pH is 6 or greater. Hydrogenase activity and synthesis are negatively regulated by alternative oxidants such as oxygen, nitrate and nitrite. Accordingly, it is possible that growth conditions of anaerobiosis, acidic pH and the absence of external oxidants are either not achieved or are achieved only slowly. Moreover, much of the lactose in the culture will have been cleaved by the time the acid- and gas-producing enzymes become active. Therefore, enzyme assays for beta-galactosidase circumvent the fermentation pathway regulation problems and yield a reporter group with every substrate cleavage event.

The presence of anaerogenic strains of genera which belong to the coliform group further complicates gas detection assay procedures. These strains possess beta-galactosidase activity, but do not produce gas from lactose. Thus, only an assay for beta-galactosidase activity would detect the anaerogenic strains of the coliform group.

It is possible to detect coliform-associated enzymes within 24 hours of incubation. Beta-galactosidase and beta-glucuronidase assay results correlate with the confirmed presence of coliforms and *E. coli*. When aliquots from 24 hour enzyme assay-positive coliform cultures are streaked onto a differential medium, such as eosin methylene blue agar, and the agar incubated, typical coliform and *E. coli* colonies are almost always recovered. Members of the coliform genera are the taxonomically identified colonies from beta-galactosidase-positive cultures. *E. coli* is the taxanomically identified organism from beta-glucuronidase-positive cultures. These observations indicate that the first incubation (presumptive) stage of the standard coliform assay can be shortened from 48 to 24 hours, and that the second (confirmed) incubation stage is unnecessary. Consequently, enzyme assays for coliforms and *E. coli* can reduce the time required to produce a confirmatory result by as much as 72 hours, and simultaneously, provide significantly better sensitivity. However, the cost is more expensive due to the reagents, especially for large sample sizes.

Food and dairy samples present problems detecting coliforms. There is a large diversity of foods and the physical/chemical nature of some makes the detection of either acidic or gaseous end products or certain types of enzyme assays difficult. For example, gas bubbles may be difficult to detect in a broth due to the turbidity from a food sample such as nonfat dried milk. The color associated with a food product such as dried cheese, chili powder or green or yellow vegetables can obscure the color of a pH indicator or a colored reporter, such as ONP, in a beta-galactosidase assay using ONPG as a substrate. Further, a food may be inherently acidic, or it may internally trap gas bubbles during sample preparation. Finally, food chemistry may interfere with an assay. Foods add additional nutrients to a culture broth and these nutrients may be metabolized by non-coliform bacteria to produce gaseous or acidic end products leading to a false-positive result. For example, cake mixes or other sweetened products contain significant amounts of disaccharides and monosaccharides, which can be converted to acid and/or gas by non-coliforms.

It is important to choose an appropriate substrate for beta-galactosidase and beta-glucuronidase assays for coliform bacterial and E. coli detection. For example, beta-galactosidase cleaves the substrate ONPG to a yellow product, ONP. However, certain colors inherent in or added to food products may obscure the yellow color of the ONP reporter product. Food substances which can obscure the yellow color include hemoglobin in red meats, chlorophyll in leafy greens and vegetables, beta-carotene and other yellow and orange pigments in fruits and vegetables, natural pigments in spices, and artificial and natural colorants. Turbid water and water with a high humic content can also obscure weakly yellow positive ONP reactions. Moreover, standard bacteriological growth media ingredients, such as protein or yeast hydrolysates, impart a yellow or golden color to the media and can obscure the presence of ONP. For example, the standard method coliform medium, lauryl sulfate tryptose (LST) broth, has a golden hue. The result of performing an ONPG-type enzyme assay in LST broth and other supplemented media will lead to a significant number of false-negative results.

An additional problem associated with the use of ONPG is the hazardous nature of the ONP cleavage product. ONP is a volatile compound and a known respiratory, eye and skin irritant. The presence of ONP makes activities associated with handling of cultures and washing of glassware hazardous to lab workers. There are also toxic waste disposal problems when using ONP.

Similarly, beta-glucuronidase assays use MUG, which generates a fluorescent signal. Pigments associated with foods have been observed to quench the fluorescent signal. For example, the pigment in chili powder obscures the fluorescence reaction of the reporter product. A further problem with MUG is that the pH range for maximal fluorescence is outside of the pH range produced during lactose fermentation. MUG is maximally fluorescent above pH 10. Yet, acids produced from lactose fermentation typically lower the coliform culture medium to pH 5 to 6, obscuring fluorescence reactions. Finally, as noted above, beta-glucuronidase assays which employ chromogenic substrates may be subject to interference from some types of samples. Therefore, current enzyme assays for beta-glucuronidase have pH and interference problems from the food samples, and are inappropriate for use in certain types of foods.

Fluorogenic substrates, such as MUG have been used in agar to detect E. coli in food samples. The fluorescent cleavage product, 4-methylumbelliferone, is soluble and will diffuse from E. coli colonies in agar (a solid medium) to add to the difficulties associated with the determination of which colonies contain the enzyme beta-glucuronidase and which do not.

An additional complication is that the final volume of culture broth for different types of samples varies from 1 ml to 1 liter. For each test, the molarity of the chromogenic or fluorogenic substrate within the culture medium would need to be constant. This would require consumption of large amounts of expensive test reagents. It would be advantageous to a food processor if all coliform testing could be done in a single assay format which features easily read results across all test samples, regardless of size, and which economizes on test reagents.

A typical food processing company or water treatment facility tests incoming and outgoing foods, process water, waste water or environmental samples. Therefore, an ONPG- or MUG-based assay may only be appropriate for certain types of samples. Thus, there is a need in the art for assays which are functional for a variety of samples, such as foods, turbid and/or colored water and environmental samples and which eliminate the difficulties associated with correlating different test methodologies.

The indogogenic substrate 5-bromo-4-chloro-3-indolyl-beta-D-galactoside (X-Gal) has been used in solid media for the detection of E. coli colonies which express beta-galactosidase activity. Beta-galactoside cleaves X-Gal to galactose and the indolyl derivative. The indolyl derivative dimerizes to form a substituted indigo, which has an intense blue color.

Frampton et al., J. Food Prot. 51:402–04, 1988, refers to a peptone-tergitol agar supplemented with 5-bromo-4-chloro-3-indolyl-$\beta$-D-glucuronide (X-Gluc) to differentiate E. coli from other bacterial colonies in artificially inoculated raw minced chicken. Ley et al., Ann. Meet., Am. Soc. Microbiol., Abstract Q35:288, 1988, refers to a method to enumerate E. coli in water and sewage using a membrane filtration technique with a glycerol medium and 3-indolyl-beta-D-glucuronide substrate. E. coli colonies appeared blue in the semisolid medium. Watkins et al., Appl. Environ. Microbiol, 54:1874–75, 1988, refers to a pour plate method using X-Gluc for detecting E. coli in shellfish and waste water.

A product Petrifilm TM (3M) uses a solid medium and X-Gluc for detecting E. coli. E. coli colonies appear blue.

Because of the high cost of the indogenic compounds X-Gal and X-Gluc, for the detection of beta-galactosidase and beta-glucuronidase activity have not found widespread use or have been used with relatively small culture volumes. Therefore, there is a need in the art for a beta-galactosidase test system that can economically use small quantities of X-Gal and X-Gluc for food and water testing, because the intense blue color will solve many of the problems associated with the yellow color of ONP and other colored reporters.

In summary, there is a need in the art, therefore, for a coliform detection assay which offers the improved sensitivity and speed associated with enzyme assays, the capacity to detect anaerogenic coliforms, successful applications to food, water and environmental samples, safety of handling and disposal, and economy in the consumption of expensive test reagents.

SUMMARY OF THE INVENTION

The present invention comprises a method for assaying an enzyme associated with a particular microorganism or a group of microorganisms and an enzyme indicator device that is useful for assaying for a particular microorganism or group of microorganisms. Preferably, the method comprises adding sample and an enzyme indicator device to growth medium, incubating at a permissive temperature and reading the results on the enzyme indicator device. Preferably, the growth medium is a liquid. Another method comprises adding a sample to a growth medium; incubating the sample and growth medium at a permissive temperature for the growth of microorganisms until there is evidence of microorganism growth within the growth medium; adding an enzyme indicator device to the growth medium, wherein the enzyme indicator device comprises a dye-forming substrate in a polymer system on a solid support, or a dye-forming substrate dried on a solid support, and wherein the dye-forming substrate is cleaved by the enzyme to form a colored precipitate; incubating the sample, growth medium, and enzyme indicator device at a permissive temperature and in an oxidizing environment from about five minutes to about five hours; and visually detecting the presence of the particular microorganism or group of microorganisms by a color change on the enzyme indicator device. Preferably, an oxidizing agent is added to the growth medium along with the enzyme indicator device. The enzyme indicator device preferably comprises a dye-forming substrate in a polymer system. Alternatively, the enzyme indicator device comprises a dye-forming substrate adhering to the surface of a solid support. More particularly, the enzyme indicator device further comprises a solid support member, wherein the dye-forming substrate in the polymer system is layered onto a surface of the solid support system. It is preferred that the solid support floats on the surface of a liquid so as to have an oxidizing environment from air without the need for additional oxidizing agents.

A further method for assaying for an enzyme associated with a particular microorganism or a group of microorganisms comprises: adding a sample to a growth medium; adding a dye-forming substrate in a polymer system, wherein the dye-forming substrate forms a precipitate in association with the polymer, when cleaved by the enzyme; contacting the dye-forming substrate in the polymer with the sample and the growth medium; incubating the sample, growth medium and dye-forming substrate in polymer at a permissive temperature for the growth of particular microorganism or group of microorganisms; and detecting the presence of the particular microorganism or group of microorganisms by a colored precipitate in association with the polymer.

The dye-forming substrate forms an insoluble precipitate upon enzymatic cleavage. Preferably, the dye-forming substrate is a substituted indigo derivative of the formula:

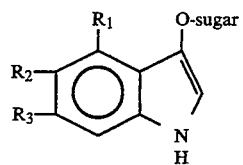

wherein each R substituent is a halo group or hydrogen. The halo group is a chloro, bromo, or iodo group. When $R_1$, $R_2$ and $R_3$ are H, the precipitate dye formed is indigo.

It is preferred that the dye-forming substrate is insoluble in aqueous systems so as to prevent the dye-forming substrate from leaching out of the polymer or from coming off the surface of the solid support when exposed to the growth medium. In this way, it is possible to conserve costs by reducing the amount of dye-forming substrate needed for each test. Thus, the amount of dye-forming substrate used is independent of the test size or the sample size. Moreover, the analysis of particular microorganisms or group of microorganisms by enzyme assays provides a more rapid and more sensitive assay system than conventional growth and pure culture detection methods.

The advantages of the inventive method and the use of the inventive enzyme indicator device allow the dye-forming substrate to be deployed on a defined reaction surface rather than dispersed throughout a solution. The reaction surface is the surface of a solid support member or a polymer matrix. This results in an assay format which is independent of culture volume, thus leading to an economy of reagent consumption. Second, the insoluble indigo dye-forming substrates from the indigogenic substrates range in color from blue to purple, colors which are not masked or quenched by pigments or turbidity associated with foods or certain types of water. Thus, the indigogenic substrates are amenable to detection of coliform bacteria in both food and water samples. Third, the indigogenic substrates offer the speed and sensitivity associated with enzyme assays. Fourth, the assay for beta-galactosidase eliminates the problems associated with enzyme-regulation in the lower portion of the lactose fermentation pathway. Fifth, an enzyme assay ensures that signal is being generated in the first step of the pathway every time the enzyme performs a hydrolysis of the dye-forming substrate, rather than at the end of the pathway where only a portion of the cleaved galactoside ends up. Lastly, the indigo reaction can be read visually, thus eliminating the need for ultraviolet illumination that is required for reading assays which employ MUG.

DETAILED DESCRIPTION OF THE INVENTION

Figure 1:
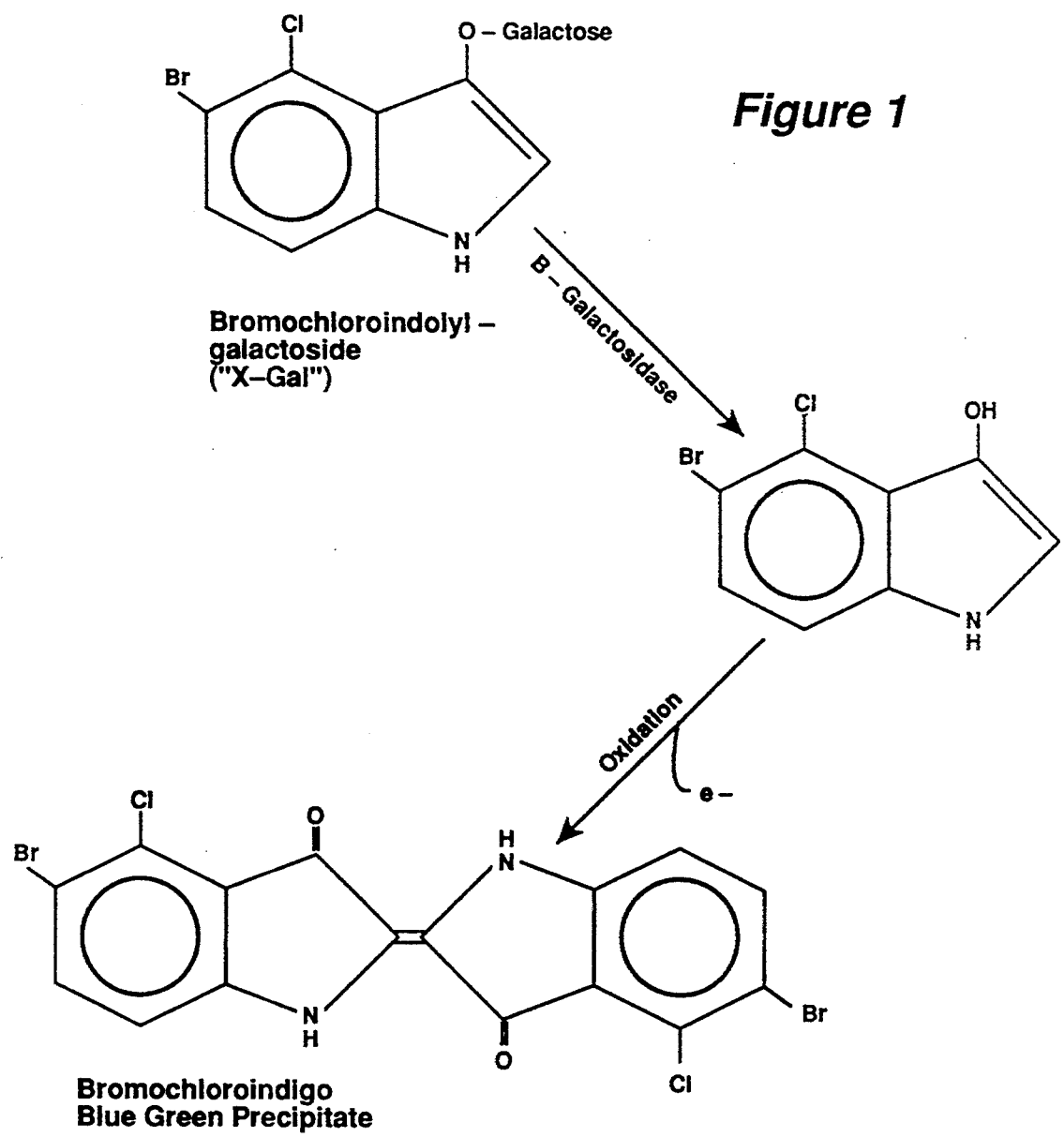
FIG. 1 shows the reaction pathway for bromochloroindolylgalactoside (X-Gal) hydrolysis to form bromochloroindigo. Bromochloroindolylgalactoside is first cleaved by beta-galactosidase from the particular microorganism or group of microorganisms to remove the galactose group and form bromochloroindoxyl, which then dimerizes by an oxidation reaction to the highly colored blue-green precipitate, bromochloroindigo. Oxidation can be achieved either by an oxidizing agent in solution or by exposure of bromochloroindoxyl to air.

The present invention is a method for assaying an enzyme associated with a particular microorganism or a group of microorganisms. Preferably, the particular microorganism is *E. coli* and the group of microorganisms is the coliform bacteria. The enzyme beta-galactosidase is characteristic of the coliform bacteria and beta-glucuronidase activity is characteristic of *E. coli*. The dye-forming substrates preferably are mixed in a polymer system and form an insoluble precipitate upon enzymatic cleavage. Alternatively, the dye-forming substrates may adhere to a solid support member which also is the reaction surface for forming the insoluble precipitate. Preferably, the dye-forming substrate is insoluble in an aqueous liquid, such as a growth medium so as to avoid dispersion of the dye-forming substrate throughout the growth medium and instead, have the dye-forming substrate concentrated within the polymer system or on the surface of the solid support member.

The reaction of the dye-forming substrate to form a highly colored precipitate requires the presence of the specific enzyme to cleave off the sugar group and an oxidizing environment to form the highly colored dimer precipitate from the cleaved dye-forming substrate. The oxidizing environment can be created by having the dye-forming substrate in the polymer exposed to air or by the addition of an oxidizing agent to the growth medium. Examples of oxidizing agents include hydrogen peroxide, $NO_3^-$, $Fe^{3+}$, $Ag^+$, pyrogallol, $Cu^+$ and others. Most preferably, the oxidizing agent will have a redox potential greater than 0.10 and be used at a concentration that avoids toxicity to the growing microorganisms.

The dye-forming substrate is preferably a substituted indigo derivative of the formula:

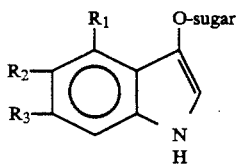

wherein each R substituent is a halo group or hydrogen. The sugar group is any monosaccharide, derivative thereof, or an aldehydo acid. Preferably, the sugar group is a galactoside or a glucoside and the aldehydo acid is glucuronic acid. Most preferably, the sugar or aldehydo acid is attached to oxygen by a beta linkage. Examples of the substituted indigo dyes include 3-indolyl-, 5-bromo-4-chloro-3-indolyl-, 5-bromo-3-indolyl-, 5-bromo-6-chloro-3-indolyl, and 5-iodo-3-indolyl- derivatives in beta-D linkages with galactose and glucuronic acid. The substrate is colorless, however when hydrolyzed by the appropriate enzyme, the indoxyl or substituted indoxyl portion of the substrate oxidizes to form an intensely colored, insoluble indigo precipitate or indigo derivative as shown, for example, in the Figure. The dimerizing reaction requires an oxidizing environment. Further, non-indigogenic beta-sugar substrates which form colored insoluble products after enzymatic cleavage could be used for the inventive method and the inventive enzyme indicator device.

In another embodiment, a culture of a particular microorganism or a group of microorganisms can grow in a growth medium or have yielded a presumptive positive result for a particular microorganism or a group of microorganisms. The inventive enzyme indicator device for assaying for a particular enzyme associated with a particular microorganism or group of microorganisms can be added to the growth medium after growth of the sample in the growth medium. For example, a dye-forming substrate can be mixed with a polymer system and then layered on top of a solid support. Alternatively, the dye-forming substrate can be adhered onto the surface of a solid support member. It is preferred that the solid support be a floatable plastic means to remain on the surface of a liquid growth medium. Alternatively, a dye-forming substrate can be mixed in with a polymer material, such as latex, to form a matrix containing the dye-forming substrate throughout. The latex matrix with dye-forming substrate can be dropped into a liquid growth medium or suspended on the surface of the liquid growth medium.

If the dye-forming substrate is not in contact with air, then a developer solution should be added to the growth medium concurrently with the dye-forming substrate or shortly thereafter. The developer solution comprises an oxidizing agent, such as hydrogen peroxide, $Ag^+$, $Hg^{++}$, $I_3^-$, $IO_4^-$, persulfate, $Pd^{++}$, nitrobenzenes, azobenzenes, quinones, 2-chloro-2-nitro-propane, $K_3Fe(CN)_6$, indolones, and p-hydroxymercaribenzoate. The developer solution preferably further comprises a precipitation enhancer and a cell permeabilizer. The cell permeabilizer facilitates entrance of an indigogenic substrate into the cell to result in a faster turnover of the substrate, and a faster exiting of the indoxyl or indigo from the bacterial cell. Examples of cell permeabilizers include, toluene, anionic and nonionic detergents, and cetyltrimethylammonium bromide. The precipitation enhancer helps to prevent the precipitate from migrating from the solid support and/or the polymer matrix. An example of a precipitation enhancer is an alkaline detergent mixture, such as sodium dodecylsulfate at a 0.1 to 1.0% concentration and a pH of 8.0 to 10.0. The precipitation enhancer is preferably used in a growth medium which shows turbidity or potential quenching of the color reaction.

The enzyme indicator device may be made by dissolving a dye-forming substrate, such as X-Gal, in a solvent such as dimethylformamide (DMF), methyl cellosolve (2-methoxyethanol), or DMSO and mixing with a liquid polymer system, such as latex. Other adhesive-type polymers that can be dried into a solid or semisolid state include, for example, ethylene vinyl acetate (EVA), polyvinyl alcohol (PVA), and polyvinyl pyrrolidone (PVP). EVA is a polymer soluble in methylene chloride. Additionally, polymer systems that can be liquefied in solvents, such as methylene chloride are useful to liquefy the adhesive-type polymer for mixing with the dye-forming substrate. The mixture of dye-forming substrate and polymer is dried to form a solid or pliable solid. Preferably, the liquid dye-forming substrate and polymer, in a more viscous state, is layered onto the surface of a solid support. Most preferably, a solid support is a porous plastic material that can float on the surface of a liquid.

Alternatively, the dye-forming substrate in solvent can be added directly to the surface of a solid support member and allowed to dry (solvent evaporated). Additionally, the dye-forming substrate can be precipitated out of the solvent, such as DMF, by adding a reagent, such as methylene chloride, in which the dye-forming substrate is insoluble. The precipitate is then layered directly onto a solid support member.

The concentration of dye-forming substrate is sufficient to produce a visible response given the surface area and volume of the reaction surface. For example, the concentration X-Gal on a circular solid support member of polyethylene with a 70 micron pore size of dimensions of one-half inch diameter and one-sixteenth thickness ranges from about 50 μg about 1 mg.

The solid support may float on the surface of a liquid, may reside below the surface of the liquid, or be mechanically placed near the surface of a liquid growth medium by physically attaching it to the culture container or culture container closure. Placing the solid support at or near the liquid-air interface offers .close proximity to oxygen in the air to facilitate the oxidation of indoxyl to indigo, thereby improving the speed and sensitivity of the assay. Further, if the solid support and ultimate color localization is located at the top of the culture medium, the reaction is not obscured by the culture broth and it becomes easier to read. If the solid support resides below the surface of the liquid, it is preferred that a developer solution be added to facilitate oxidation of the dye-forming substrate.

When testing for coliform bacteria, common components in the medium, such as in LST broth, can obscure the color reaction from a soluble substrate such as ONPG. Thus, ONPG can only be tested in clear media so that weak reactions can be read. Here, the incorporation of the dye-forming substrate onto a solid support of literally any size can conserve reagent use independent of sample size. The same solid support and surface area of dye-forming substrate associated with a polymer system can be used for any volume of culture, because the substrate reaction with the bacterial enzyme takes place within a defined surface area rather than throughout the entire volume of the culture. The blue color which is generated is not obscured by ordinary bacteriological media components and therefore an assay with the dye-forming substrate in a polymer system can be performed in a complex medium such as LST broth. The insoluble blue precipitate that is formed from hydrolysis of the dye-forming substrate in the presence of an oxidizing environment remains at the surface of the solid support, thus concentrating the reaction product into a comparatively small, more readily-observed space. Localization of the precipitate makes the test easier to read and increases its sensitivity. The localization of the enzyme assay to a solid support also results in an economy of reagent use.

In another aspect, the inventive method and enzyme indicator device can be used in a quantitative assay to estimate the number of coliform bacteria in a food or water sample using the most probable number (MPN) method. An MPN coliform assay is performed by incorporating a dye-forming substrate in a polymer system, such as latex into a standard coliform medium, such as LST broth. Preparation of the sample is done by standard techniques. After 24 hours of incubation, the tubes are read for color production in the polymer system and the positive tubes are used to calculate a confirmed MPN per gram or MPN per milliliter value, according to standard MPN techniques. See *Compendium of Methods for the Microbiological Examination of Foods* (2nd Ed., American Public Health Association, 1984), *Official Methods of Analysis* (14th Ed., Association of Official Analytical Chemists, 1984), and *Standard Methods for the Examination of Water and Wastewater* (17th Ed., American Public Health Association, 1981).

Moreover, the inventive method and enzyme indicator device are used, for example, for qualitative testing for coliform bacteria. An indigogenic galactoside substrate is incorporated into the medium used for the PA test for coliforms in drinking water. The water sample is added to a medium containing the dye-forming substrate in a polymer system, preferably layered onto a floatable plastic solid support. Precipitated indigo, on the solid support member, within the culture vessel after a suitable incubation period signifies the presence of coliforms in the sample. This procedure is also used for qualitative testing of environmental samples for the presence of coliforms. For example, a surface or drain could be assayed for the effectiveness of sanitation by swabbing with a cotton-tipped applicator and then placing the applicator in a coliform medium containing the indigogenic galactoside dye-forming substrate incorporated into a polymer system, preferably on a solid support member. A precipitated indigo color within the culture vessel, or more specifically on the surface of the solid support after a suitable incubation period, such as 1 to 24 hours at a permissive temperature for bacterial growth would signify the presence of coliforms in the sample.

The following examples are offered by way of illustration and not by way of limitation.

EXAMPLE 1

This example illustrates a method for detecting coliform bacteria in drinking water by the PA (presence-absence) technique, as described in *Standard Methods for the Examination of Water and Wastewater*, (17 th Ed., American Public Health Association, 1981). Briefly, 100 ml of water are aseptically added to 50 ml of triple strength Clark's medium in a 250 ml bottle. Clark's medium had been modified to exclude a pH indicator. After inoculation, a plastic support containing an indigogenic galactoside substrate in a latex polymer system was added to the culture vessel so that it floated at the liquid surface. The indigogenic galactoside substrate in a latex polymer system on the plastic support was made as described herein. The mixture was incubated at 35°° C. and the plastic support was inspected for indigo formation at 24 hours.. The indigo-positive reaction signified the confirmed presence of coliforms in the water sample.

EXAMPLE 2

This example illustrates a method for detecting coliform bacteria and *E. Coil* in an environmental sample using the inventive method. The environmental sample was taken in an effort to assess the effectiveness of sanitation or as part of a routine environmental screening program. A cotton-tipped applicator was wetted with sterile diluent and used to swab a surface. The swab was placed in a bacteriological lauryl sulfate tryptose broth growth medium. A buoyant circular plastic support layered with an indigogenic galactoside substrate in a polymer system on one-half of the circle and an indigogenic glucuronide substrate on the other half of the circle was added after inoculation. The mixture was incubated for 35° C. for 24 hours. An indigo-positive reaction on one half of the plastic support signified the presence of coliform bacteria in the environmental sample. An indigo-positive reaction on both halves of the plastic support signified the presence of *E. coli* in the sample.

EXAMPLE 3

This example illustrates a method for estimating the level of coliforms and *E. coli* in a food or water sample by the Most Probable Number (MPN) analysis using the inventive method. The MPN technique is described in *Compendium of Methods for the Microbiological Examination of Foods* (2nd Ed., American Public Health Association, 1984), *Official Methods of Analysis* (14th Ed., Association of Official Analytical Chemists, 1984), and *Standard Methods for the Examination of Water and Wastewater* (17th Ed., American Public Health Association, 1981).

Water samples (10 ml) were aseptically added to 10 ml of double-strength lauryl sulfate tryptose (LST) broth. A buoyant circular plastic solid support containing an indigogenic galactoside substrate in a polymer system on one-half of the circular plastic and an indigogenic glucuronide substrate in a polymer system on the other half was added to each test tube after inoculation. The mixture was incubated at 35° C. for 24 hours. An indigo-positive reaction on one half of the plastic support signifies the confirmed presence of coliform bacteria in the water sample. An indigo-positive reaction on both halves of the plastic support confirms the presence of *E. coli* in the sample. The number of indigo-positive cultures was used to estimate the number of coliform bacteria and *E. coli* present within the original water sample through the use of a standard statistical probability table (MPN Table).

The food samples were diluted in serial 10-fold fashion prior to the MPN assay. One part (by mass) of solid food sample was added to 9 parts (by volume) of sterile diluent Butterfield's buffered phosphate buffer. The mixture was blended at high speed for two minutes. Two additional 10-fold dilutions were made from the 1:10 diluted food sample. One ml of each 10-fold dilution was added to each of three 10 ml test tubes of LST broth. A buoyant circular plastic support containing an indigogenic galactoside substrate in a polymer system on one half and an indigogenic glucuronide substrate in a polymer system on the other half was added to each test tube after inoculation. The mixture was incubated at 35° C. for 24 hours. An indigo-positive reaction on one half of the plastic support confirmed the presence of coliform bacteria in the sample dilution. An indigo-positive reaction on both halves of the plastic support confirmed the presence of *E. coli* in the sample dilution. The number of indigo-positive cultures was used to estimate the number of coliform bacteria and *E. coli* present within the original food sample through the use of standard statistical probability tables (MPN Table).

EXAMPLE 4

This example illustrates a method for the confirmation of presumptively positive coliform cultures for total coliforms and for *E. coli* using an indigogenic substrate mixture. Cultures which were presumptively gas-positive for coliforms were confirmed for coliform and/or *E. coli* presence according to the following procedure. A buoyant circular solid support containing an indigogenic galactoside substrate on one half and an indigogenic glucuronide substrate on the other half was added to the culture. An oxidizing agent (hydrogen peroxide at 10% concentration) was added to the culture. The presumptive portion of the coliform MPN analysis was performed in LST broth on a food or water sample using the procedure described in Example 3. Cultures which were gas-positive after 24 to 48 hours of incubation were confirmed with the buoyant, circular solid support described herein along with the addition of a developer comprising the oxidizing agent. The culture was incubated at 35° C. for approximately one hour and the plastic support was read for indigo formation. Cultures which were indigo-positive on one half of the circular solid support were considered to be confirmed for the presence of coliform bacteria. Cultures which were indigo-positive on both halves of the circular solid support were confirmed for the presence of *E. coli*. Negative cultures were reincubated for an additional hour and reread. Cultures which were still negative for indigo at two hours remained unconfirmed for the presence of coliforms or *E. coli*.

Although the foregoing invention has been described, in part, by way of illustration and example for the purposes of clarity and understanding, it will be apparent that certain changes or modifications may be practiced without deviating from the spirit and scope of the invention.

We claim:

1. A method for assaying for an enzyme associated with a particular species of microorganism or a group of microorganisms in a sample, wherein the particular species of microorganism is *E. coli* and the group of microorganisms is the coliform group of bacteria comprising:

incubating in a single vessel the sample, a liquid growth medium and an enzyme indicator device at a permissive temperature for the growth of *E. coli* or the coliform group of bacteria, the sample selected from the group consisting of a water sample, a food sample, and an environmental sample, and the enzyme indicator device comprising a dye-forming substrate that is specific for the enzyme and that is located at a surface of a solid support, wherein the substrate, forms an insoluble precipitate when cleaved by the enzyme and is a substituted indigo derivative of the formula:

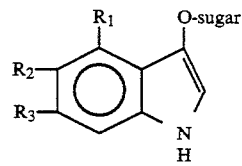

wherein each R substituent is a halo group or hydrogen and wherein the sugar is selected from the group consisting of glucuronide, glucoside, and galactoside; and detecting in said single vessel the presence of the *E. coli* or the coliform group of bacteria by a colored insoluble precipitate on the solid support.

2. The method of claim 1 wherein the halo group is selected from the group consisting of chloro, bromo, and iodo.

3. The method of claim 1 wherein the enzyme indicator device consists essentially of a layer of one or more dye-forming substrates adhering to the solid support.

4. The method of claim 3 wherein the solid support comprises a disc, and the layer of one or more dye-forming substrates consists essentially of X-gal on a first portion of a first side of the disc and X-gluc on a second portion of the first side of the disc.

5. The method of claim 1 wherein the method is able to detect a single initial cell of the particular microorganism or group of microorganisms in the sample within about 24 hours.

6. The method of claim 1 wherein the method consists essentially of said steps of incubating and detecting.

7. An enzyme indicator device for assaying for the presence of either the species *E. coli* or the coliform group of bacteria consisting essentially of one or more dye-forming substrates adhered to a surface of a solid support wherein the one or more substrates are cleaved by an enzyme associated with *E. coli* or the coliform group of bacteria to form an insoluble colored precipitate located at the reaction surface, and wherein the dye-forming substrate is a substituted indigo derivative of the formula:

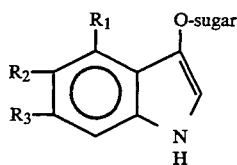

wherein each R substituent is a halo group or hydrogen and wherein the sugar is selected from the group consisting of glucuronide, glucoside, and galactoside.

8. The enzyme indicator device of claim 7 wherein the enzyme indicator device consists essentially of a first dye-forming substrate on a first portion of the solid support and a second dye-forming substrate on a second portion of the solid support.

9. The enzyme indicator device of claim 8 wherein the first dye-forming substrate is X-gal, and wherein the second dye-forming substrate is X-gluc.

10. The enzyme indicator device of claim 7 wherein the halo group is selected from the group consisting of chloro, bromo, and iodo.

11. An enzyme indicator device for assaying for the presence of either the coliform group of bacteria or for the species *E. coli* consisting essentially of a first dye-forming substrate and a second dye-forming substrate, each of the formula:

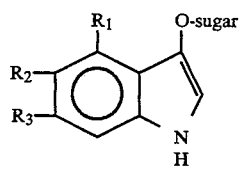

wherein each R substituent is a halo group or hydrogen and the sugar is selected from the group consisting of glucuronide, glucoside, and galactoside, the first dye-forming substrate and the second dye-forming substrate each adhered to different portions of a surface of a solid support, the solid support able to float on a liquid and having a color that contrasts with each of the products resulting from cleavage of each of the first dye-forming substrate and second dye-forming substrate by an enzyme associated with *E. coli* or the coliform group of bacteria.

12. The enzyme indicator device of claim 11 wherein the halo group is selected from the group consisting of chloro, bromo, and iodo.

13. The enzyme indicator device of claim 11 wherein the device is able to detect the presence of a single, metabolically active initial *E. coli* or cell of the coliform group of bacteria in about 24 hours.

14. The enzyme indicator device of claim 11 wherein the solid support is white.

15. The enzyme indicator device of claim 11 wherein the first dye-forming substrate is X-gal, and wherein the second dye-forming substrate is X-gluc.

* * * * *

UNITED STATES PATENT AND TRADEMARK OFFICE
CERTIFICATE OF CORRECTION

PATENT NO. : 5,403,721

DATED : April 4, 1995

INVENTOR(S) : N. Robert Ward, Jr. et al.

It is certified that error appears in the above-identified patent and that said Letters Patent is hereby corrected as shown below:

In column 14, claim 1, line 40, please delete ",".

Signed and Sealed this

Twenty-ninth Day of August, 1995

Attest:

BRUCE LEHMAN

Attesting Officer     Commissioner of Patents and Trademarks